United States Patent
Stubbs et al.

(10) Patent No.: US 9,603,549 B2
(45) Date of Patent: Mar. 28, 2017

(54) IMPLANTABLE DEVICE WITH POST-MRI CARDIAC SIGNAL SENSING ADJUSTMENT

(75) Inventors: Scott R. Stubbs, Maple Grove, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1373 days.

(21) Appl. No.: 12/917,101

(22) Filed: Nov. 1, 2010

(65) Prior Publication Data

US 2011/0160602 A1    Jun. 30, 2011

Related U.S. Application Data

(60) Provisional application No. 61/291,012, filed on Dec. 30, 2009.

(51) Int. Cl.
  *A61B 5/0402*  (2006.01)
  *A61B 5/06*    (2006.01)
  *A61N 1/37*    (2006.01)
  *A61N 1/08*    (2006.01)

(52) U.S. Cl.
  CPC ............... *A61B 5/063* (2013.01); *A61N 1/37* (2013.01); *A61N 1/3704* (2013.01); *A61B 2560/0271* (2013.01); *A61B 2560/0276* (2013.01); *A61N 2001/086* (2013.01)

(58) Field of Classification Search
  USPC .......................................... 607/62; 600/509
  See application file for complete search history.

(56) References Cited

U.S. PATENT DOCUMENTS

| | | | |
|---|---|---|---|
| 4,516,579 A * | 5/1985 | Irnich ............................... | 607/9 |
| 6,678,560 B1 | 1/2004 | Gilkerson et al. | |
| 6,937,906 B2 * | 8/2005 | Terry et al. ..................... | 607/63 |
| 7,242,981 B2 * | 7/2007 | Ginggen ......................... | 607/27 |
| 7,363,080 B2 | 4/2008 | Stubbs et al. | |
| 7,373,200 B2 | 5/2008 | Stubbs et al. | |
| 7,483,744 B2 | 1/2009 | Stubbs et al. | |
| 7,509,167 B2 | 3/2009 | Stessman | |
| 7,515,955 B2 | 4/2009 | Linder et al. | |
| 2006/0293591 A1 * | 12/2006 | Wahlstrand et al. ......... | 600/423 |
| 2007/0150010 A1 | 6/2007 | Stubbs et al. | |
| 2007/0238975 A1 * | 10/2007 | Zeijlemaker .................. | 600/411 |
| 2007/0239231 A1 * | 10/2007 | Ginggen ......................... | 607/63 |
| 2009/0138058 A1 | 5/2009 | Cooke et al. | |
| 2009/0157127 A1 | 6/2009 | Sowder et al. | |

(Continued)

OTHER PUBLICATIONS

Mollerus, Michael, et al., "Cardiac Biomarkers in Patients with Permanent Pacemakers and Implantable Cardioverter-Defibrillators Undergoing an MRI Scan", PACE, vol. 31, (Oct. 2008), 1241-1245.

(Continued)

*Primary Examiner* — Carl H Layno
*Assistant Examiner* — Erin M Piateski
(74) *Attorney, Agent, or Firm* — Schwegman Lundberg & Woessner, P.A.

(57) ABSTRACT

An implantable device, such as a pacer, defibrillator, or other cardiac rhythm management device, can include an automatic testing and adjusting of cardiac signal sensing after an MRI scanning procedure, such as to accommodate an MRI-induced physiological change in sensed cardiac depolarization amplitude or in lead impedance such as at an electrode/tissue interface.

17 Claims, 2 Drawing Sheets

(56) References Cited

U.S. PATENT DOCUMENTS

2009/0157146 A1    6/2009  Linder et al.

OTHER PUBLICATIONS

Mollerus, Michael, et al., "Ectopy in Patients with Permanent Pacemakers and Implantable Cardioverter-Defibrillators Undergoing an MRI Scan", PACE, vol. 32, (Jun. 2009), 772-778.

Mollerus, Michael E., et al., "Magnetic Resonance Imaging of Pacemakers and Implantable Cardioverter-Defibrillators Without Specific Absorption Rate Restriction", HES Conference, (May 15, 2009), 1 pg.

Stubbs, et al., "Implantable Medical Device Responsive to MRI Induced Capture Threshold Changes", U.S. Appl. No. 2/568,433, filed Sep. 28, 2009.

* cited by examiner

IMPLANTABLE DEVICE WITH POST-MRI CARDIAC SIGNAL SENSING ADJUSTMENT

CLAIM OF PRIORITY

This application claims the benefit of priority under 35 U.S.C. §119(e) of U.S. Provisional Patent Application Ser. No. 61/291,012, entitled "IMPLANTABLE DEVICE WITH POST-MRI CARDIAC SIGNAL SENSING ADJUSTMENT", filed on Dec. 30, 2009, which is herein incorporated by reference in its entirety.

BACKGROUND

Implantable medical devices (IMDs) can perform a variety of diagnostic or therapeutic functions. For example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), or cardiac resynchronization therapy (CRT) devices, among others. Nuclear magnetic resonance imaging (MRI) is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

In a MR field, an item, such as an IMD, can be referred to as "MR Safe" if the item poses no known hazard in all MRI environments. In an example, MR Safe items can include non-conducting, non-metallic, non-magnetic items, such as a glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement or torque, heating, induced current or voltage, or one or more other factors. An item known to pose hazards in all MRI environments, such as a ferromagnetic scissors, can be referred to as "MR Unsafe."

OVERVIEW

An implantable device, such as a pacer, defibrillator, or other cardiac rhythm management device, can include an automatic testing and adjusting of cardiac signal sensing after an MRI scanning procedure, such as to accommodate an MRI-induced physiological change in sensed cardiac depolarization amplitude or in lead impedance such as at an electrode/tissue interface.

Example 1 can include or use an ambulatory or implantable medical device comprising: a cardiac signal sensing circuit; and a controller circuit, coupled to the cardiac signal sensing circuit, the controller configured to receive an indication that a magnetic resonance imaging (MRI) scanning procedure has completed and, in response, to automatically test a cardiac signal sensing of the cardiac signal sensing circuit, and to adjust a cardiac signal sensing parameter when a physiological change in depolarization amplitude or lead impedance causes a post-MRI scanning procedure loss of cardiac depolarization sensing.

In Example 2, the subject matter of Example 1 can optionally be configured such that the implantable medical device comprises an MR-mode, and wherein the indication that the MRI scanning procedure has completed comprises a transition from the MR-mode.

In Example 3, the subject matter of any one of Examples 1-2 can optionally be configured such that the implantable medical device comprises an MRI detector circuit, coupled to the controller circuit, the MRI detector circuit configured to detect whether an MRI scanner device is present near the implantable medical device, and wherein the MRI detector circuit is configured to use information about whether the MRI scanner is present near the implantable medical device to provide the indication that the MRI scanning procedure has completed.

In Example 4, the subject matter of any one of Examples 1-3 can optionally be configured such that the indication that the MRI scanning procedure has completed is based on information about a detected fault condition associated with an MRI scanning procedure.

In Example 5, the subject matter of any one of Examples 1-4 can optionally comprise a communication module, coupled to the controller circuit, wherein the communication module is configured to communicate from the implantable medical device a report indicative of a cardiac signal sensing parameter that was automatically altered in response to post-MRI scanning procedure testing of the cardiac signal sensing.

In Example 6, the subject matter of any one of Examples 1-5 can optionally comprise a communication module, coupled to the controller circuit, wherein the communication module is configured to communicate from the implantable medical device an alert indicative of loss of cardiac signal sensing after the MRI scanning procedure.

In Example 7, the subject matter of any one of Examples 1-6 can optionally comprise the controller being configured to repeatedly automatically test the cardiac signal sensing over a period of time associated with post-MRI scanning procedure physiological variability of a cardiac signal amplitude or lead impedance.

Example 8 can include, or can be combined with the subject matter of any one of Examples 1-6 to optionally comprise an ambulatory or implantable medical device comprising: a cardiac signal sensing circuit; and a controller circuit, coupled to the cardiac signal sensing circuit, the controller configured to receive an indication that a magnetic resonance imaging (MRI) scanning procedure has completed and, in response, to automatically test a cardiac signal sensing of the cardiac signal sensing circuit, and to adjust a cardiac signal sensing parameter when a physiological change in depolarization amplitude or lead impedance causes a post-MRI scanning procedure loss of cardiac depolarization sensing; and a communication circuit, coupled to the controller circuit, wherein the communication circuit is configured to communicate from the implantable medical device at least one of: a report indicative of a cardiac signal sensing parameter that was automatically altered in response to post-MRI scanning procedure testing of the cardiac signal sensing; or, an alert indicative of loss of cardiac signal sensing after the MRI scanning procedure; and wherein the indication that the MRI scanning procedure has completed comprises at least one of a transition from an MR-mode of the implantable medical device; information from an MRI detector circuit; and information about a detected fault condition.

In Example 9, the subject matter of any one of Examples 1-8 can optionally comprise a local external interface device, configured to be communicatively coupled with the implantable medical device, the local external interface device configured to receive a report indicative of a cardiac signal sensing parameter that was automatically altered in response to post-MRI scanning procedure testing of the cardiac signal sensing; or, an alert indicative of loss of cardiac signal sensing after the MRI scanning procedure.

In Example 10, the subject matter of any one of Examples 1-9 can optionally comprise a local external interface device, configured to be communicatively coupled with the implantable medical device, the local external interface device configured to receive an alert indicative of loss of cardiac signal sensing after the MRI scanning procedure.

In Example 11, the subject matter of any one of Examples 1-10 can optionally comprise a remote external interface device, configured to be communicatively coupled with the implantable medical device, the remote external interface device configured to receive a report indicative of a cardiac signal sensing parameter that was automatically altered in response to post-MRI scanning procedure testing of the cardiac signal sensing; or, an alert indicative of loss of cardiac signal sensing after the MRI scanning procedure.

In Example 12, the subject matter of any one of Examples 1-11 can optionally comprise a remote external interface device, configured to be communicatively coupled with the implantable medical device, the remote external interface device configured to receive an alert indicative of loss of cardiac signal sensing after the MRI scanning procedure.

Example 13 can include, or can be combined with the subject matter of any one of Examples 1-12 to optionally comprise: receiving an indication that a magnetic resonance imaging (MRI) scanning procedure has completed; and in response to the MRI scanning procedure completion, automatically testing a cardiac signal sensing of an implantable medical device; and when a physiological change in depolarization amplitude or lead impedance causes a post-MRI scanning procedure loss of cardiac depolarization sensing, adjusting a cardiac signal sensing parameter of the implantable medical device to help re-establish cardiac depolarization sensing.

In Example 14, the subject matter of any one of Examples 1-13 can optionally comprise determining MRI scanning procedure completion by detecting a switch from an MR-mode.

In Example 15, the subject matter of any one of Examples 1-14 can optionally comprise determining MRI scanning procedure completion using a MRI scanner detector circuit that is configured to detect when an MRI scanner is present near the implantable medical device.

In Example 16, the subject matter of any one of Examples 1-15 can optionally comprise determining MRI scanning procedure completion by detecting a fault condition associated with an MRI scanning procedure.

In Example 17, the subject matter of any one of Examples 1-16 can optionally comprise communicating to a user a report indicative of a cardiac signal sensing parameter that was automatically altered in response to post-MRI scanning procedure testing of the cardiac signal sensing.

In Example 18, the subject matter of any one of Examples 1-17 can optionally comprise communicating to a user an alert indicative of loss of cardiac signal sensing after the MRI scanning procedure.

In Example 19, the subject matter of any one of Examples 1-18 can optionally comprise repeating the automatically testing the cardiac signal sensing over a period of time associated with post-MRI scanning procedure physiological variability of a cardiac signal amplitude or lead impedance.

In Example 20, the subject matter of any one of Examples 1-19 can optionally comprise declaring MRI scanning procedure completion in response to: detecting a switch from an MR-mode; detecting when an MRI scanner is no longer present near the implantable medical device; and detecting a fault condition associated with an MRI scanning procedure.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

1. MRI Overview

Figure 1:
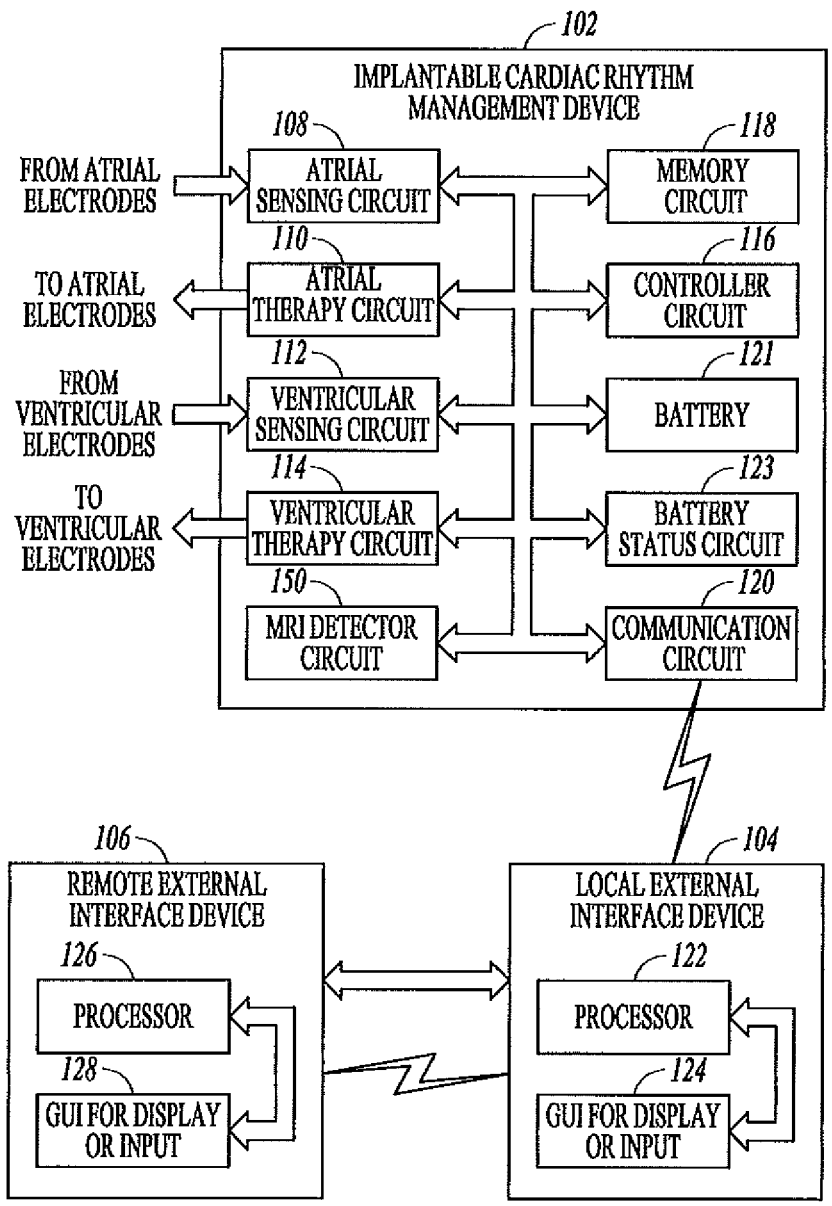
FIG. 1 illustrates an example of portions of a cardiac function management system and an environment in which it is used.

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during MR, such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field allows a volume or plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment—because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during defibrillation shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which $\varepsilon$ can represent the electromotive force (e.g., in volts), such as developed by a time-varying magnetic flux. The magnetic flux can be represented as $$\Phi_{B_1} = \int\int_S B_1 \cdot dS,$$

in which $B_1$ can represent an instantaneous magnetic flux density vector (e.g., in Webers per square meter, or Tesla). If $B_1$ is relatively uniform over the surface S, then the magnetic flux can be approximately $\Phi_{B_1} = |B_1||A|$, where A can represent the area of the surface S. Operating MRI equipment can produce a time-varying gradient field having a slew rates in excess of 100 Tesla per second (T/s). The slew rate can be similar to a "slope" of the gradient field, and is thus similar to $$\frac{d\Phi_{B_1}}{dt}.$$

The electromotive force (EMF) of Faraday's law can cause an unwanted heating effect in a conductor—regardless of whether the conductor is ferromagnetic. EMF can induce current flow in a conductor (e.g., a housing of an IMD, one or more other conductive regions within an IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can dissipate heat. The induced heat can cause a significant temperature rise in or near the conductor over the duration of the scan. The power dissipated by the eddy current can be proportional to the square of both the peak flux density and the frequency of the excitation.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the EMF can create, among other things, non-physiologic voltages that can cause erroneous sensing of cardiac electrical activity, or the EMF can create a voltage sufficient to depolarize cardiac tissue or render the cardiac tissue refractory, possibly affecting pacing therapy. In an illustrative example, an IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the electromotive force (EMF) developed through the body tissue between the electrode (e.g., a distal tip or ring electrode) of the lead and the housing of the IMD can be more than 0.03 square meters times 100 t/s, or more than 3 volts.

2. System Overview

FIG. 1 illustrates an example of portions of a cardiac function management system 100 and an environment in which it is used. In certain examples, the system 100 includes an implantable cardiac rhythm or function management device 102, a local external interface device 104, and an optional remote external interface device 106. In certain examples, the implantable device 102 includes an atrial sensing circuit 108, an atrial therapy circuit 110, a ventricular sensing circuit 112, a ventricular therapy circuit 114, a controller circuit 116, a memory circuit 118, a communication circuit 120, a power source such as a battery 121, and a battery status circuit 123.

The atrial sensing circuit 108 is typically coupled to electrodes, such as an intra-atrial electrode or any other electrode that permits sensing of an intrinsic atrial cardiac signal including atrial depolarization information. The atrial therapy circuit 110 is typically similarly coupled to these or other electrodes, such as for delivering pacing, cardiac resynchronization therapy (CRT), cardiac contractility modulation (CCM) therapy, defibrillation/cardioversion shocks, or other energy pulses to one or both atria.

The ventricular sensing circuit 112 is typically coupled to electrodes, such as an intra-ventricular electrode or any other electrode that permits sensing of an intrinsic ventricular cardiac signal including ventricular depolarization information. The ventricular therapy circuit 114 is typically similarly coupled to these or other electrodes, such as for delivering pacing, cardiac resynchronization therapy (CRT), cardiac contractility modulation (CCM) therapy, defibrillation/cardioversion shocks, or other energy pulses one or both ventricles.

A controller circuit 116 is coupled to the atrial sensing circuit 108 and the ventricular sensing circuit 112 to receive information from the sensed cardiac signals, and is coupled to the atrial therapy circuit 110 and the ventricular therapy circuit 114 to provide control or triggering signals to trigger timed delivery of the therapy pulses. In an example, the controller circuit 116 can be configured to provide control to help permit the therapy to be effectively delivered, such as in combination with one or more other therapies (e.g., bradycardia pacing, antitachyarrhythmia pacing (ATP), cardiac resynchronization therapy (CRT), atrial or ventricular defibrillation shock therapy) or functionalities (e.g., auto-threshold functionality for automatically determining pacing threshold energy, autocapture functionality for automatically adjusting pacing energy to capture the heart, etc.). In an example, this can include providing dedicated modules within the controller circuit 116, or providing executable, interpretable, or otherwise performable code configure the controller circuit 116.

A memory circuit 118 is coupled to the controller circuit 116, such as to store control parameter values, physiological data, or other information. A communication circuit 120 is coupled to the controller circuit 116 to permit radiofrequency (RF) or other wireless communication with an external device, such as the local external interface device 104 or the remote external interface device 106.

In an example, the battery 121 can include one or more batteries to provide power for the implantable device 102. In an example, the battery 121 can be rechargeable, such as by wireless transcutaneous power transmission from an external device to the implantable device 102. The battery status circuit 123 can be communicatively coupled to each of the battery 121 and the controller circuit 116, such as to determine battery status information, for example, indicative of how much energy remains stored in the battery 121. The controller circuit 116 can be configured to alter operation of the implantable device 102, such as based at least in part on the battery status information.

The local external interface device 104 typically includes a processor 122 and a graphic user interface (GUI) 124 or like device for displaying information or receiving user input as well as a communication circuit, such as to permit wired or wireless communication with the remote external interface device 106 over a communications or computer network. Similarly, the remote external interface device 106 typically includes a processor 126 and a graphic user interface (GUI) 128 or like device for displaying information or receiving user input as well as a communication circuit, such as to permit wired or wireless communication with the local external interface device 104 over the communications or computer network. Because the system 100 includes processing capability in the implantable device 102 (e.g., provided by the controller circuit 116), the local external interface device 104 (e.g., provided by the processor 122), and the remote external interface device 106 (e.g., provided by the processor 126), various methods discussed in this document can be implemented at any of such locations, or tasks can be distributed between two or more of such locations.

The present inventors have recognized, among other things, that when the implantable device 102 resides in a subject that is undergoing an MRI scanning procedure, it may be possible for current flow in the leadwires coupling the electrodes to the electronics unit to generate local heating of tissue, such as at the interface region between the electrodes and cardiac tissue. The degree of tissue heating can be related to factors such as the length of the leadwire, the conductivity or impedance of the leadwire, or the surface area of the electrodes, which are typically located at the distal end of the leadwire. It is believed that such heating can cause an acute change in the pacing threshold energy required to capture a resulting heart contraction. A system and method for accommodating MRI-induced changes in capture threshold is described in Stubbs et al. U.S. patent application Ser. No. 12/568,433 entitled IMPLANTABLE MEDICAL DEVICE RESPONSIVE TO MRI INDUCED CAPTURE THRESHOLD CHANGES, which was filed on Sep. 28, 2009, and which is assigned to Cardiac Pacemakers, Inc., which is incorporated by reference herein in its entirety, including its description of a system and method of accommodating MRI-induced changes in capture threshold.

It is also believed by the present inventors that such MRI-induced heating can cause an acute change in the cardiac signal sensing threshold needed to appropriately detect a desired cardiac electrogram signal artifact (e.g., P-wave, R-wave, etc.), such as a cardiac depolarization that is indicative of a heart contraction. An acute change in the cardiac depolarization signal amplitude or lead impedance is believed to be a physiological effect resulting from the local heating of tissue at the electrode/tissue interface due to the MRI scanning procedure, which can be distinct from MRI-induced effects on the sensing circuitry itself. It is believed that this acute physiological change in the cardiac depolarization signal amplitude or lead impedance at the electrode/tissue interface can persist for several hours after the MRI scanning procedure.

For example, if the MRI scanning procedures shifts the amplitude of an intrinsic cardiac depolarization artifact from above the corresponding fixed sensing threshold value to below the corresponding fixed sensing threshold value, then such intrinsic contractions may not be detected by the implantable device 102. In an example, for a bradyarrhythmia patient for which the implantable device 102 is providing a pacer function, such an amplitude shift can result in asynchronous delivery of pacing pulses to the patient, rather than inhibiting delivery of a pacing pulse when an intrinsic cardiac depolarization artifact is sensed during an escape interval that is being timed by a timer circuit to control the paced heart rate. The present inventors have recognized that by adjusting gain or fixed sensing threshold of the cardiac signal sensing circuitry of the implantable device 102 to accommodate any acute physiological changes in the cardiac signal depolarization amplitude, such asynchronous pacing can be avoided, which can improve the quality of pacing therapy being delivered to the patient. The present inventors have also recognized that in an implantable device 102 that employs an automatic gain control (AGC) circuit (rather than a fixed-gain, fixed sensing threshold circuit), one or more parameters associated with the AGC circuit can also be adjusted, post-MRI scanning procedure, such as to better accommodate an acute physiological change in the cardiac signal depolarization amplitude.

To adjust cardiac sensing in response to an MRI-scanning procedure, the implantable device 102 can include the memory circuit 118 being configured with an MR-mode storage location, indicating whether the implantable device 102 is in an operating mode compatible with an MRI scanning procedure.

In an example, the implantable device 102 can be placed into the MR-mode by local or remote programming by a user, such as via the communication circuit 120. For example, the user can locally or remotely program the implantable device 102 of a patient into the MR-mode before the patient undergoes a scheduled MRI scanning procedure. In an example, the user can locally or remotely program the implantable device 102 of the patient out of the MR-mode and back into a non-MR-mode after the MRI scanning procedure has been complete. In an example, the implantable device 102 can revert from the MR-mode to the non-MR-mode after a specified time period (e.g., associated with an MRI scanning procedure) has elapsed since being placed into the MR-mode. In an example, both user-programming and the elapsing of a specified time period can be used as conjunctive or disjunctive conditions to switch the implantable device 102 from the MR-mode to the non-MR mode after an MRI scanning procedure.

In an example, the implantable device 102 can include an MRI detector circuit 150 such as to detect a magnetic field associated with an MRI scanner being near the implantable device 102. Examples of the MRI detector 150 can include a reed switch, a Hall-effect sensor, an inductor saturation detector, a magnetotransistor, a magnetodiode, a magneto-optical sensor, or a giant magnetoresistive sensor, or any combination of these. In an example, a mode switch from the non-MR mode to the MR-mode can be triggered by the MRI detector 150 indicating that an MRI scanner is present. In an example, a mode switch from the MR-mode back to the non-MR mode can be triggered by the MRI detector 150 (either alone, or in combination with a timer, such as described above) indicating that an MRI scanner is no longer present.

In an example, the MRI detector circuit 150 can include a Hall-effect sensor, such as to detect the presence of an MR field indicative of an MR scanner performing an MR scanning operation nearby. An example of using a Hall effect sensor in an implantable medical device to sense a magnetic field is described in Linder et al. U.S. Patent Pub. No. 20090157146, entitled IMPLANTABLE MEDICAL DEVICE WITH HALL SENSOR, assigned to Cardiac Pacemakers, Inc., which is incorporated herein by reference in its entirety, including its description of using a Hall-effect sensor to detect a magnetic field, such as that of an MRI scanner. An example of using a Hall-effect sensor in conjunction with an MRI operating mode of an implantable medical device is described in Cooke et al. U.S. Patent Pub. No. 20090138058, entitled MRI OPERATION MODES FOR IMPLANTABLE MEDICAL DEVICES, which is assigned to Cardiac Pacemakers, Inc., which is incorporated herein by reference in its entirety, including its description of using a Hall-effect sensor in conjunction with an MRI operating mode of an implantable medical device.

In an example, the MRI detector circuit 150 can additionally or alternatively include an inductor saturation detector, such as to detect the presence of an MR field indicative of an MR scanner performing an MR scanning operation nearby. An example of using inductor saturation to perform MRI detection is described in Stessman, U.S. Pat. No. 7,509,167, entitled MRI DETECTOR FOR AN IMPLANTABLE MEDICAL DEVICE, assigned to Cardiac Pacemakers, Inc., which is incorporated herein by reference in its entirety, including its description of using inductor saturation to perform MRI detection.

In an example, adjusting cardiac sensing in response to an MRI-scanning can be performed when the MR-mode storage location indicates that the implantable device 102 is exiting or has just exited the MR-mode. In an example, adjusting cardiac sensing in response to an MRI-scanning can be triggered by an indirect indicator of possible MRI-scanning, such as by the detecting of a specified fault-condition that can be associated with an MRI-scanning procedure. Some examples of fault conditions that can result from an MRI-scanning procedure can include a system reset, a watchdog timer fault, a multi-bit memory error, transitioning from control under the primary controller 116 to control under a back-up safety core, the controller 116 improperly switching between different threads of programming code, oscillator faults, detecting high-rate pacing, etc.

Illustrative examples of an implantable device, such as an implantable cardiac rhythm management device, such as including a primary controller and a fail-safe backup safety core are described in:

Stubbs et al., U.S. Pat. No. 7,363,080, entitled SYSTEM AND METHOD FOR PROVIDING BRADYCARDIA THERAPY BY IMPLANTABLE DEVICE IN PRESENCE OF SYSTEM FAULTS, assigned to Cardiac Pacemakers, Inc., which is incorporated herein by reference in its entirety, including is description of systems and methods using a safety core, such as for providing bradycardia therapy;

Stubbs et al., U.S. Pat. No. 7,373,200, entitled SYSTEM AND METHOD FOR PROVIDING TACHYARRHYTHMIA THERAPY BY IMPLANTABLE DEVICE IN PRESENCE OF SYSTEM FAULTS, assigned to Cardiac Pacemakers, Inc., which is incorporated herein by reference in its entirety, including its description of systems and methods using a safety core, such as for providing tachyarrhythmia therapy;

Stubbs et al., U.S. Pat. No. 7,483,744, entitled SYSTEM AND METHOD FOR RECOVERING FROM TRANSIENT FAULTS IN AN IMPLANTABLE MEDICAL DEVICE, assigned to Cardiac Pacemakers, Inc., which is incorporated herein by reference in its entirety, including its description of systems and methods using a safety core;

Stubbs et al., U.S. Patent Publication No. US 2007/0150010 A1, entitled CARDIAC PACEMAKER WITH PACING RATE MONITORING, which was filed on Dec. 22, 2005, assigned to Cardiac Pacemakers, Inc., which is incorporated herein by reference in its entirety, including its description of systems and methods configured to operate in multiple rate monitoring zones to inhibit or prevent excessively high-rate pacing during a particular mode of device operation; and Sowder et al., U.S. Patent Publication No. US 2009/0157127 A1, entitled TELEMETRY DURING SAFETY MODE OPERATION, which was filed on Dec. 4, 2008, assigned to Cardiac Pacemakers, Inc., which is incorporated by reference herein in its entirety, including its description of systems and methods such as for allowing communication between an IMD and an external device during safety mode operation.

Also, an illustrative example of a limited functionality safe back-up mode of operation, such as an electrosurgery mode, is described in Gilkerson et al. U.S. Pat. No. 6,678,560 entitled CARDIAC RHYTHM MANAGEMENT SYSTEM WITH ELECTROSURGERY MODE, which is assigned to Cardiac Pacemakers, Inc., and which is incorporated by reference herein in its entirety, including its description of systems and methods for providing limited functionality during a safe back-up mode of operation, such as during electrosurgery.

Figure 2:
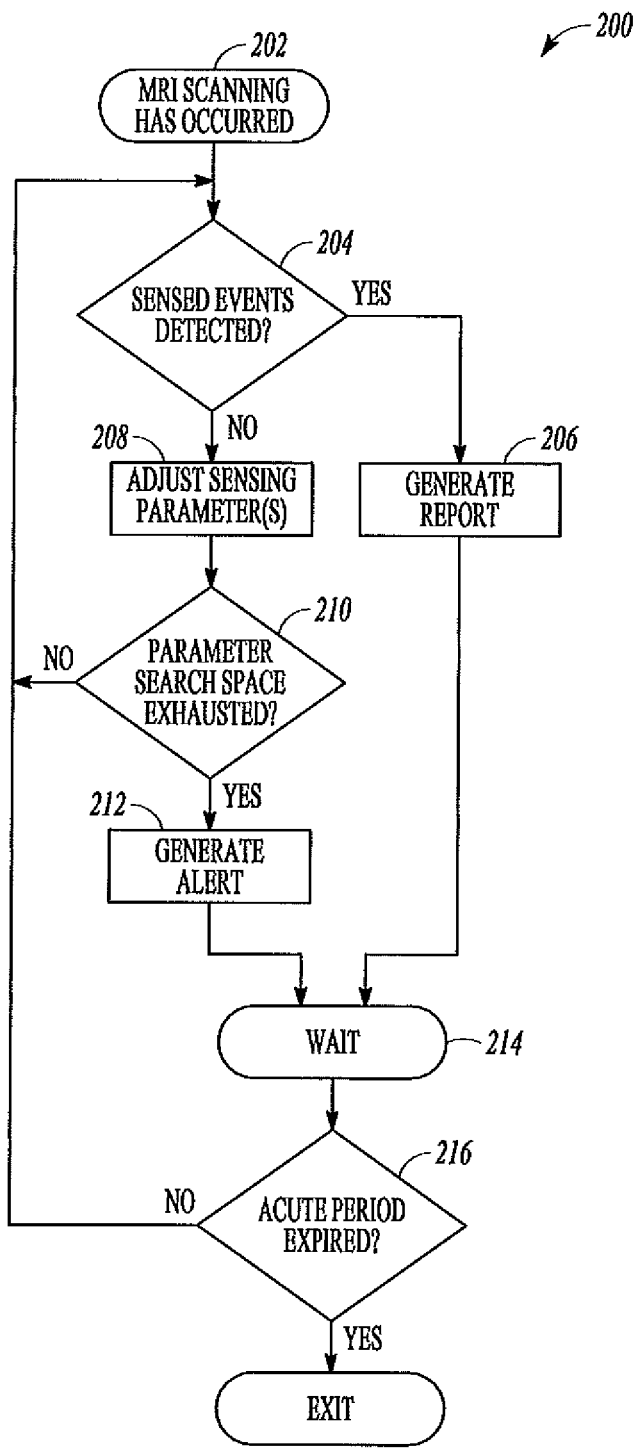
FIG. 2 shows an example of adjusting a parameter of sensing an electrical cardiac signal, such as in response to completing an MRI scanning procedure

FIG. 2 shows an example 200 of adjusting a parameter of sensing an electrical cardiac signal, such as in response to completing an MRI scanning procedure, such as can be determined as explained above. At 202, it can be determined that an MRI scanning procedure has been completed, such as by detecting a transition from an MR-mode to a non-MR-mode, by detecting a timer expiration, by detecting cessation of an MRI seamier field using the MRI detector circuit 150, by detecting a fault indirectly indicative of MRI scanner exposure, or the like.

At 204, an electrical cardiac signal sensing test can be initiated, such as using a specified post-MRI electrode configuration. In an example, this can include determining whether sensed events indicative of cardiac depolarizations can be detected using then-current parameter settings (e.g., one or more of fixed sensing threshold value, fixed sensing amplifier gain, AGC threshold decay rate, AGC threshold decay step-size, AGC threshold floor, AGC gain increase rate, AGC gain increase step-size, AGC gain ceiling, AGC delay from detected peak to onset of threshold decay or onset of gain increase, etc.).

In an AGC example, one or more of the sensing threshold value or sensing amplifier gain can be variable. In an AGC example, the gain or threshold can be controllably varied during an interval between successive cardiac events (e.g., one or more paced events or intrinsic events), such as according to a specified gain or threshold "template." In an example, the variable sensing threshold or gain template can include a piecewise linear approximation of a geometric progression, such as an approximation to an exponential decay curve, or including one or more other shapes. For example, the post-MRI cardiac signal sensing testing can include determining one or more parameters of a dynamic sensing threshold or gain template, such as determining one or more of a gain increase rate, gain increase step-size, an initial gain value, a gain ceiling, a sensing threshold decrease rate, a sensing threshold decrease step-size, an initial sensing threshold value, a sensing threshold minimum, a delay from a detected cardiac event to an onset of a threshold decrease or a gain increase, etc.

Various techniques can be used to determine whether a candidate sensed cardiac depolarization event should be deemed an actual sensed cardiac depolarization event. In an example, a dynamic noise estimation can be performed, and a candidate sensed cardiac depolarization event can be deemed an actual sensed cardiac depolarization event when the amplitude of a filtered cardiac signal exceeds the detection threshold, such as described in Linder et al., U.S. Pat. No. 7,515,955, filed on Nov. 7, 2006, assigned to Cardiac Pacemakers, Inc., which is incorporated herein by reference in its entirety. In an example, an independent sensor can be used to detect heart contractions (e.g., pressure sensor, heart sound sensor, intracardiac impedance sensor, thoracic impedance sensor), and information from the independent sensor can be signal-processed and used to confirm whether a candidate sensed cardiac depolarization event should be deemed an actual sensed cardiac depolarization event.

At 204, if a specified number (e.g., a fixed number, X of Y candidate events) of candidate events are deemed actual sensed cardiac depolarization events, then at 206, a report indicating the same can be generated and communicated via the communication circuit 120, such as to the local external interface device 104, which, in turn, can communicate the report to the remote external interface device 106. The report can include the then-current sensing parameters, such as in the event any of the sensing parameters were altered to accommodate post-MRI scanning procedure cardiac signal amplitude or lead impedance values. This can help alert a user to an operational change to the implantable device 102, based on an automatic determination by the implantable device 102. In an example, the implantable device 102 can request user-approval of any such changes before they are put into effect, however, this is not required.

At 204, if an insufficient number of candidate events are detected or deemed other than actual sensed cardiac depolarization events, then at 208, one or more cardiac signal sensing parameters can be adjusted. In an example, this can include decreasing a fixed threshold value to which a candidate sensed cardiac signal event is compared to determine whether it should be deemed an actual sensed cardiac depolarization event. In an example, the adjusting can include increasing a fixed gain of the sensing circuit used to detect the cardiac signal including any cardiac depolarizations. In an example, the adjusting can include adjusting one or more AGC parameters, filtering or other signal processing parameters or the like.

At 208, after the parameter adjusting, provided that the parameter search space has not been exhausted, at 210, process flow can return to 204, such as to determine whether sensed events can be better detected using the one or more adjusted parameter values. At 210, if the parameter search space has been exhausted, then at 212 an alert can be generated and communicated via the communication circuit 120, such as to the local external interface device 104, which, in turn, can communicate the report to the remote external interface device 106. This can help alert a caregiver or other user that, post-MRI, a suitable set of sensing parameters could not be automatically determined by the implantable device 102. In an example, generating the alert 212 can be accompanied by placing implantable device 102 into a specified back-up mode of operation to enhance safety until the patient can been seen by a physician.

It is believed that the acute response of sensed cardiac depolarization amplitude or lead impedance to an MRI scanning procedure can vary, such as over a period of several hours, or up to several days following the MRI scanning procedure. Therefore, it can be desirable to optionally repeat the test after a specified waiting period (e.g., after a specified time period such as of a duration that is between 1-4 hours, inclusive) at 214. Before repeating testing of sensing, however, at 216 it can be determined whether a specified acute time period over which the sensing amplitude or lead impedance can be expected to vary (e.g., between 1-3 days, inclusive) has expired. If so, the process can exit at 218, otherwise, the process can return to 204 to re-test sensing. In an example, a process similar to that shown in FIG. 2 can be performed for various different sensing channels (e.g., atrial, right ventricular, left ventricular, etc.) or for various different electrode configurations (e.g., unipolar, bipolar, LV-multipolar, etc.).

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus comprising:
an ambulatory or implantable medical device comprising:
  a cardiac signal sensing circuit; and
  a controller circuit, coupled to the cardiac signal sensing circuit, the controller configured to receive an indication that a magnetic resonance imaging (MRI) scanning procedure has completed and, in response, to automatically test a cardiac signal sensing of the cardiac signal sensing circuit, and to automatically adjust and then automatically use the adjusted cardiac signal sensing parameter when a physiological change in depolarization amplitude or lead impedance causes a post-MRI scanning procedure loss of cardiac depolarization sensing.

2. The apparatus of claim 1, wherein the implantable medical device comprises an MR-mode, and wherein the indication that the MRI scanning procedure has completed comprises a transition from the MR-mode.

3. The apparatus of claim 1, wherein the implantable medical device comprises an MRI detector circuit, coupled to the controller circuit, the MRI detector circuit configured to detect whether an MRI scanner device is present near the implantable medical device, and wherein the MRI detector circuit is configured to use information about whether the MRI scanner is present near the implantable medical device to provide the indication that the MRI scanning procedure has completed.

4. The apparatus of claim 1, wherein the indication that the MRI scanning procedure has completed is based on information about a detected fault condition associated with an MRI scanning procedure.

5. The apparatus of claim 1, comprising a communication module, coupled to the controller circuit, wherein the communication module is configured to communicate from the implantable medical device a report indicative of a cardiac signal sensing parameter that was automatically altered in response to post-MRI scanning procedure testing of the cardiac signal sensing.

6. The apparatus of claim 1, comprising a communication module, coupled to the controller circuit, wherein the communication module is configured to communicate from the implantable medical device an alert indicative of loss of cardiac signal sensing after the MRI scanning procedure.

7. The apparatus of claim 1, wherein the controller is configured to repeatedly automatically test the cardiac signal sensing over a period of time associated with post-MRI scanning procedure to test physiological variability of a cardiac signal amplitude or lead impedance.

8. An apparatus comprising:
an ambulatory or implantable medical device comprising:
a cardiac signal sensing circuit; and
a controller circuit, coupled to the cardiac signal sensing circuit, the controller configured to receive an indication that a magnetic resonance imaging (MRI) scanning procedure has completed and, in response, to automatically test a cardiac signal sensing of the cardiac signal sensing circuit, and to automatically adjust and then automatically use the adjusted cardiac signal sensing parameter when a physiological change in depolarization amplitude or lead impedance causes a post-MRI scanning procedure loss of cardiac depolarization sensing; and
a communication circuit, coupled to the controller circuit, wherein the communication circuit is configured to communicate from the implantable medical device at least one of: a report indicative of a cardiac signal sensing parameter that was automatically altered in response to post-MRI scanning procedure testing of the cardiac signal sensing; or, an alert indicative of loss of cardiac signal sensing after the MRI scanning procedure; and
wherein the indication that the MRI scanning procedure has completed comprises at least one of:
a transition from an MR-mode of the implantable medical device;
information from an MRI detector circuit; and
information about a detected fault condition.

9. The apparatus of claim 8, comprising:
a local external interface device, configured to be communicatively coupled with the implantable medical device, the local external interface device configured to receive a report indicative of a cardiac signal sensing parameter that was automatically altered in response to post-MRI scanning procedure testing of the cardiac signal sensing; or, an alert indicative of loss of cardiac signal sensing after the MRI scanning procedure.

10. The apparatus of claim 8, comprising:
a local external interface device, configured to be communicatively coupled with the implantable medical device, the local external interface device configured to receive an alert indicative of loss of cardiac signal sensing after the MRI scanning procedure.

11. The apparatus of claim 8, comprising:
a remote external interface device, configured to be communicatively coupled with the implantable medical device, the remote external interface device configured to receive a report indicative of a cardiac signal sensing parameter that was automatically altered in response to post-MRI scanning procedure testing of the cardiac signal sensing; or, an alert indicative of loss of cardiac signal sensing after the MRI scanning procedure.

12. The apparatus of claim 8, comprising:
a remote external interface device, configured to be communicatively coupled with the implantable medical device, the remote external interface device configured to receive an alert indicative of loss of cardiac signal sensing after the MRI scanning procedure.

13. An apparatus comprising:
an ambulatory or implantable medical device comprising:
a cardiac signal sensing circuit; and
a controller circuit, coupled to the cardiac signal sensing circuit, the controller configured to receive an indication that a magnetic resonance imaging (MRI) scanning procedure has completed and, in response, to automatically test a cardiac signal sensing of the cardiac signal sensing circuit, and to automatically adjust and then automatically use the adjusted cardiac signal sensing parameter when a physiological change in depolarization amplitude or lead impedance causes a post-MRI scanning procedure loss of cardiac depolarization sensing; and
a communication circuit, coupled to the controller circuit, wherein the communication circuit is configured to communicate from the implantable medical device at least one of: a report indicative of a cardiac signal sensing parameter that was automatically altered in response to post-MRI scanning procedure testing of the cardiac signal sensing; or, an alert indicative of loss of cardiac signal sensing after the MRI scanning procedure; and
wherein the indication that the MRI scanning procedure has completed comprises:
a transition from an MR-mode of the implantable medical device;
information from an MRI detector circuit; and
information about a detected fault condition.

14. The apparatus of claim 13, comprising:
a local external interface device, configured to be communicatively coupled with the implantable medical device, the local external interface device configured to receive a report indicative of a cardiac signal sensing parameter that was automatically altered in response to post-MRI scanning procedure testing of the cardiac signal sensing; or, an alert indicative of loss of cardiac signal sensing after the MRI scanning procedure.

15. The apparatus of claim 13, comprising:
a local external interface device, configured to be communicatively coupled with the implantable medical device, the local external interface device configured to receive an alert indicative of loss of cardiac signal sensing after the MRI scanning procedure.

16. The apparatus of claim 13, comprising:
a remote external interface device, configured to be communicatively coupled with the implantable medical device, the remote external interface device configured to receive a report indicative of a cardiac signal sensing parameter that was automatically altered in response to post-MRI scanning procedure testing of the cardiac signal sensing; or, an alert indicative of loss of cardiac signal sensing after the MRI scanning procedure.

17. The apparatus of claim 13, comprising:
a remote external interface device, configured to be communicatively coupled with the implantable medical device, the remote external interface device configured to receive an alert indicative of loss of cardiac signal sensing after the MRI scanning procedure.

* * * * *